United States Patent [19]

Dixon et al.

[11] Patent Number: 4,813,964
[45] Date of Patent: Mar. 21, 1989

[54] CROSSLINKED ANISOTROPIC XENOGENEIC DIAPHRAGM TISSUE IN FLEXOR TENDON PULLEY RECONSTRUCTION

[75] Inventors: France T. Dixon, San Clemente, Calif.; Royce C. Lewis, Jr., Lubbock, Tex.

[73] Assignee: Hancock Jaffe Laboratories, Irvine, Calif.

[21] Appl. No.: 925,108

[22] Filed: Oct. 14, 1986

[51] Int. Cl.$^4$ .............................................. A61F 2/08
[52] U.S. Cl. ....................................... 623/13; 623/11; 623/66; 8/94.11; 8/94.19 R; 128/DIG. 8; 128/898
[58] Field of Search ................ 8/94.1, 94.11, 94.19 R, 8/94.20; 128/DIG. 8, 1 R; 623/1, 2, 11, 13, 66

[56] References Cited

U.S. PATENT DOCUMENTS

| | | | |
|---|---|---|---|
| 4,120,649 | 10/1978 | Schechter | 623/66 |
| 4,239,492 | 12/1980 | Holman et al. | 8/94.11 |
| 4,388,735 | 6/1983 | Ionescu et al. | 623/2 |
| 4,440,833 | 8/1983 | Kurland | 623/13 |

*Primary Examiner*—Richard J Apley
*Assistant Examiner*—Paul Prebilic
*Attorney, Agent, or Firm*—Grant L. Hubbard

[57] ABSTRACT

A xenogeneic tissue replacement for nonfunctional flexor tendon pulley comprising crosslinked, bovine or porcine or other anisotropic mammalian diaphragm and method of use are disclosed.

2 Claims, No Drawings

CROSSLINKED ANISOTROPIC XENOGENEIC DIAPHRAGM TISSUE IN FLEXOR TENDON PULLEY RECONSTRUCTION

CROSS-REFERENCE TO RELATED APPLICATION

The invention disclosed and claimed herein is a species of the invention described in U.S. patent application Ser. No. 918,032 which discloses the use of crosslinked anisotropic xenogeneic diaphragm tissue in surgery generally, the present invention involving the discovery that most surprising and advantageous results are obtained using said tissue in flexor tendon pulley reconstruction.

FIELD OF THE INVENTION

This invention relates to xenogeneic tissue implantation in human tissue repair and prostheses.

BACKGROUND OF THE INVENTION

Implantation in humans of xenogeneic tissue, i.e. tissue from a species other than human, has been carried on extensively for more than two decades. Xenogeneic implants are useful in replacing human tissues which are damaged by pathological or traumatic injury. Such implants have been used for replacing heart valves, ligaments, tendons and skin, for example. Many techniques for preparation and treatment of xenogeneic tissue have been developed for many types of prosthetic and tissue repair applications in the human body. For example, treatment of such tissue with collagen in various forms and degrees of denaturization are known (U.S. Pats. Nos. 3,563,228, Seiderman, 3,949,073, Daniels et al, and 4,233,360, Luck, et al.) Treatment of graft tissues with aldehydes, and glutaraldehyde in particular, is well known (see, for example, U.S. Pat. Nos. 3,988,872, Dardik, et al., which is but one of many disclosures of the use of glutaraldehyde in tissue treatment.)

Exemplary of the state of the art are the following U.S. Pats. Nos.: Angell et al, Nos. 4,035,848 and 4,247,292 and Hancock, et al, No. 4,050,893—glutaraldehyde treatment of porcine heart valves; Schechter, No. 4,120,649—glutaraldehyde treatment of pigskin, human tissue, and amniotic membranes; Holman, et al, Nos. 4,239,492 and 4,240,794—glutaraldehyde treatment of umbilical cord tissue for vascular grafts; Ketharanathan, No, 4,319,363—glutaraldehyde treatment of artificially induced tubular structure of collagenous tissue; Lentz et al, No. 4,323,358—treatment of implant tissue with glutaraldehyde and wetting agent; Wright, No. 4,350,492, and Lane, Nos. 4,372,743 and 4,443,895—heart valve prosthesis from glutaraldehyde treated porcine heart valve; Kurland, No. 4,400,833—tendons and ligaments from cows and pericardium or other porcine tissue treated with glutaraldehyde and reinforced with synthetic mesh structure; Pollock, et al, No. 4,402,697—treatment of implant tissue with phosphate ester and glutaraldehyde; and Pollock, No. 4,405,327—treatment of implant tissue with quaternary ammonium compounds and glutaraldehyde.

The fibro-osseous sheath of the hand flexor tendon is composed of thickened areas of arced fibers (annular pulleys), alternating with crisscrossed fibers (cruciate pulleys). The function of the pulleys is to enhance flexor tendon gliding function by holding the tendons close to the phalanges to prevent them from "bowstringing" during flexion and extension.

Flexor tendon function relies on two factors: (1) tendon excursion and (2) forces that resist tendon gliding. Loss of the fibro-osseous pulleys not only alters the resistive forces but also changes the excursion of the tendon necessary to flex a digit.

There are, of course, many prosthetic and repair materials available. Synthetic materials, such as Teflon ™, dacron, Nitex ™, and xenogeneic tissue or allograft tissue such as bovine or porcine pericardia, fascia lata, and the like have been suggested as flexor tendon pulley repair materials.

Synthetics tend to be unduly bulky or thick, and can cut into the tendon, and can also result in a high inflammatory response due to particulate abrasion. Uncrosslinked or insufficiently crosslinked xenogeneic tissue and allograft tissue may lose mechanical properties as a result of rapid tissue remodeling under the stress of use, with a return of the pre-operative problems and symptoms. Available crosslinked xenogeneic tissues, such a bovine or porcine pericardial tissue, do not possess the necessary properties for the repair of structures characterized by high pressure and relative movement and thus stretch and allow adhesion formation.

An improved xenogeneic tissue is disclosed as the present invention which solves or greatly mitigates the problems prevalent in the prior art.

SUMMARY OF THE INVENTION

An implant material which is constructed, dimensioned and adapted to replace nonfunctional flexor tendon pulleys in the surgical repair of the hand, and a method of preparing and using the same are disclosed as the present invention.

A particular implant material comprising appropriately sized graft of sterilized bovine or porcine or other anisotropic mammalian diaphragm which has been cross-linked has been found to be more effective in restoring the function of degenerated flexor tendon pulleys and has been found to be effective for a longer period of time than was the case with any prior art xenogeneic tissue, as well as being free of the inflammatory tendencies of some synthetic repair materials.

The invention contemplates a xenogeneic tissue replacement for nonfunctional flexor tendon pulleys of a degenerated human hand tendon system comprising crosslinked, sterile bovine or porcine or other anisotropic mammalian diaphragm, and a method of tissue replacement for nonfunctional flexor tendon pulleys comprising surgical removal of the nonfunctional flexor tendon pulleys and replacing the same with such diaphragm fomred as flexor tendon pulley replacement grafts.

DESCRIPTION OF THE PREFERRED EMBODIMENT

Bovine or porcine or other anisotropic mammalian diaphragm is obtained, stripped of nonessential tissue and cleaned according to standard techniques used in obtaining xenogeneic tissue. The diaphragm is cross-linked using known methods. The diaphragm is characterized by having one very smooth serous side, and one rough, fibrous side, the importance of which structure will be apparent as the method of use is described.

As illustrated by the previously cited prior art, glutaraldehyde has been reported as being effective in reducing antigenicity and reducing the likelihood of infection. Glutaraldehyde crosslinks proteins rapidly and effectively, and causes the cross-linking of proteins in the tissue being treated. This treatment increases resistance to proteolytic cleavage and hence increases resistance to enzymatic degradation. The treatment of implant tissue with glutaraldehyde is sometimes referred to as "tanning" because it crosslinks the protein and inhibits enzymatic and biochemical degradation of the tissue, comparable in general to the effect of tanning leather. Glutaraldehyde is also often used as the preservative in aqueous solution for storing tissues after treatment.

Crosslinking of the protein in the tissue may be accomplished in a number of ways and any crosslinking reagent may be used. Glutaraldehyde is one of the preferred reagents. Other aldehydes, however, or other crosslinking materials may be used. The crosslinking can be carried out in any desired method. Many such methods are described in the prior art. Generally, the crosslinking step comprises soaking the tissue in glutaraldehyde solution, or other aldehyde containing solution, for from a few minutes to several days, depending upon the rate of crosslinking reaction. The rate of crosslinking reaction can be controlled by controlling the concentration of glutaraldehyde and, to a lesser extent, by controlling the pH and/or the temperature of the crosslinking reagent. The concentration of the glutaraldehyde is typically from about 0.1% to 5.0% The solution is typically buffered to about pH 7 to 9 with any suitable buffer, e.g. conventional bicarbonate, citrate, and phosphate buffers and the like. Time and concentration are, of course, related and considerable variation in both are well known in the art. The solution may include one or a number of crosslinking materials, such as, for example, formaldehyde, glyoxal,and/or dialdehyde starch. This step is, of course, well known and reference may be made to any number of prior art patents and publications for guidance as to this step. For example, one well known treatment method for crosslinking tissue, i.e. crosslinking the proteins in the tissue, is described by Yarbrough, et al; Structural alterations in tissue cardiac valves implanted in patients and in calves., *J Thoracic and Cardiovascular Surgery*, March 1973, pp. 364-74.

Generally cleaned bovine or porcine or other anisotropic mammalian diaphragm tissue, prepared by removal of fat and foreign tissue and trimmed in the usual manner to form membrane layers, each having a smooth serous side and a rough fibrous side. The membrane is then soaked, either free-floating or in a fixed configuration as desired, in glutaraldehyde solution, as described hereinbefore, and in the prior art, such as, for example, in Yarbrough et al, supra. The crosslinked mammalian diaphragm is sterilized, if necessary, and is washed thoroughly to remove all traces of unreacted glutaraldehyde and other chemicals used in preparation.

The appropriately sized graft of crosslinked diaphgram is utilized over the flexor tendon in the area of the excised, damaged pulley, with the smooth side down over the flexor tendon, and is stitched onto the underside of the phalanx either directly to itself or onto the periosteum. The surgery is conducted and completed in accordance with usual surgical procedures.

By way of illustration, and not of limitation, a simple example of the present invention is given, with the caution that adaptations and adjustments may be made without departing from the invention. Fresh bovine or porcine diaphragm tissue is received from the slaughterhouse, inspected to meet vendor specifications, and thoroughly rinsed in pH 7.4 phosphate buffered solution. The diaphragm tissue is dissected, separating and discarding all fat tissue and extraneous connective tissue and blood vessels, to leave only a smooth serous side and a fibrous side. The fibrous side is thinned down to a maximum of 0.5 mm using pathology scalpels. The dissected tissue is cut into smaller pieces of usable areas. This tissue is submerged in a suitable container of 0.2% phosphate buffered glutaraldehyde pH 7.4 and kept at room temperature. The submerged tissue is laid flat in the container and left unstressed. The container is kept closed to eliminate the possiblilty of contamination to the tissues, and Good Laboratory Practice Regulations and Good Manufacturing Practice Regulations are followed at all phases of the process. After 24 hours has elapsed, the tissue is turned and the solution discarded and fresh 0.2% buffered glutaraldehyde is added until the tissue is completely submerged. This procedure is repeated at 48 and 72 hours. After 72 to 96 hours, samples of the crosslinked tissue are tested using standard Shrinkage Temperature testing apparatus and procedures to assure adequate crosslinking. The crosslinked tissue is aseptically dissected to final configuration under sterile environment, such as, for example, a Class 100 Laminar Flow Bench. The final configuration of the pulley replacement material should normally be about 10 mm wide, 20 mm long and 0.3 to 04. mm thick, though the exact dimensions will depend upon the particular patient and procedure for which the tissue is being prepared. Dimensioning is accomplished using a fine scalpel for dissection to meet particular size requirements. In preparing tissues for sale or distribution, a series of tissues ranging from about 7 mm×12 mm to about 15 mm×30 mm in width and length are prepared thus permitting the surgeon to select the appropriate size. The surgeon can, of course, modify a given size to meet a particular requirement as determined during surgery. The tissue is inspected by Quality Assurance to assure compliance with all specifications, packaged in an approved container of sterile physiologic saline and radiation sterilized.

The biocompatable cross linked bovine or porcine or other anisotropic mammalian diaphragm allows host connective tissue to ingrow the outer fibrous layer while the inner smooth layer allows unobstructed gliding of the flexor tendon with minimal adhesion formation. The method of this invention si simplified because of the ease of surgical implant. The result of the surgery performed in accordance with this invention is superior to known prior art methods because of the characteristics of the crosslinked, anisotropic mammalin diaphragm, which is characterized in that it has a smooth serous side riding against the tendon providing a high strength wear and degradation resistant surface to protect and permit movement of the flexor tendon, and a rough or fibrous side which promotes tissue in-growth into the fibrous side of the diaphragm material thereby increasing the compliance and performance of the reconstructd pulley.

INDUSTRIAL APPLICATION

The tissues of the invention are suitable for shipment and sale as human implants.

What is claimed is:

1. A method of tissue replacement for nonfunctional flexor tendon pulleys comprising replacing said flexor tendon pulleys with anisotropic, crosslinked mammalian diaphragm which is characterized in that said diaphragh has one smooth side and one fibrous side, the smooth side being placed against the flexor tendon.

2. A method of tissue replacement for nonfunctional flexor tendon pulleys comprising replacing said flexor tendon pulleys with anisotropic, crosslinked bovine or porcine diaphragm which is characterized in that said diaphragh has one smooth side and one fibrous side, the smooth side being placed against the flexor tendon.

* * * * *